(12) United States Patent
Minotti (10) Patent No.: US 7,875,001 B2
(45) Date of Patent: Jan. 25, 2011

(54) MULTI MEDICATION NASAL SPRAY DEVICE AND METHOD

(76) Inventor: Americo Michael Minotti, 868 Pat Nixon Rd., State Road, NC (US) 28676

( * ) Notice: Subject to any disclaimer, the term of this patent is extended or adjusted under 35 U.S.C. 154(b) by 85 days.

(21) Appl. No.: 12/072,177

(22) Filed: Feb. 25, 2008

(65) Prior Publication Data

US 2009/0216183 A1 Aug. 27, 2009

(51) Int. Cl.
*A61M 37/00* (2006.01)
*B67D 7/70* (2010.01)

(52) U.S. Cl. .................. 604/82; 604/83; 604/311; 604/310; 604/38; 604/151; 604/152; 222/137; 222/145.5

(58) Field of Classification Search .............. 604/311, 604/94.01, 191, 82, 83, 310, 38, 151, 152; 128/206.11, 200.14; 222/94, 135, 136, 145.5, 222/137
See application file for complete search history.

(56) References Cited

U.S. PATENT DOCUMENTS

| | | | | |
|---|---|---|---|---|
| 2,973,883 | A | * | 3/1961 | Modderno .................... 222/94 |
| 4,355,739 | A | | 10/1982 | Vierkotter |
| 4,826,048 | A | * | 5/1989 | Skorka et al. ................ 222/137 |
| 4,949,874 | A | * | 8/1990 | Fiedler et al. ................ 222/135 |
| 4,950,237 | A | | 8/1990 | Henault et al. |
| 5,005,736 | A | | 4/1991 | Portas |
| 5,224,627 | A | * | 7/1993 | Weag ........................... 222/135 |
| 5,411,176 | A | * | 5/1995 | Favre ............................ 222/94 |
| 5,439,141 | A | | 8/1995 | Clark et al. |
| 5,857,591 | A | | 1/1999 | Bachand |
| 5,875,931 | A | | 3/1999 | Py |
| 6,082,588 | A | | 7/2000 | Markey et al. |
| 6,516,795 | B1 | * | 2/2003 | Bougamont et al. ..... 128/200.14 |
| 6,729,560 | B2 | | 5/2004 | Foster et al. |
| 7,060,732 | B2 | | 6/2006 | Vishnupad et al. |
| 7,311,693 | B2 | | 12/2007 | Shekalim |

* cited by examiner

*Primary Examiner*—Nicholas D Lucchesi
*Assistant Examiner*—Leah Stohr
(74) *Attorney, Agent, or Firm*—Robert W. Pitts (57) ABSTRACT

A nasal spray apparatus for simultaneously administrating metered amounts of multiple medicaments includes chambers for separately storing incompatible medicaments, such as an antihistamine and a steroid. Reciprocal piston pumps allow the medications to be sprayed into the user's nasal cavity. Two pumps can be used to separately transfer the medicaments to a receptacle where they can be initially mixed just prior to administration. A small volume receptacle is used to reduce the amount of mixture remaining after each stroke of the nasal spray apparatus. A check valve can be associated with each pump to further reduce medicament mixtures from cross contamination within storage chamber preparations. Collapsible components, including collapsible storage chambers or balloon capacitors can be employed to compensate for vacuums and back pressures as the medicaments are pumped to a spray nozzle.

11 Claims, 7 Drawing Sheets

MULTI MEDICATION NASAL SPRAY DEVICE AND METHOD

FIELD OF THE INVENTION

The present invention relates to dispensing devices and methods for administering medicaments. More particularly, the present invention relates to devices and methods which are well suited for use as nasal spray devices and methods for separately preserving and simultaneously delivering two or more medicaments for treating illnesses or conditions through the nasopharyngeal region.

BACKGROUND OF THE INVENTION

For many years physicians have treated allergies and other medical conditions by employing the use of nasal sprays. As pharmaceutical allergy care has advanced over the years, so has the delivery system of these pharmaceutical agents. Efforts have been directed at targeting sites topically which have lead to improvements in therapeutic efficacy and reduced systemic side effects. There has been research and development relating to the use of combinations of active ingredients as well. Of course, in some cases it may be desired to administer a drug in combination with another drug to take advantage of a synergistic effect between the two drugs. However, this approach can be problematic if the two drugs cannot be stored together because of an incompatibility problem.

For example, aqueous preparations of nasal steroids and antihistamines have been utilized in modern allergy care with great success. Recent investigations and observations from clinicians have noted a synergistic effect demonstrating improved outcomes when using both product classes consecutively. However, attempts to combine the two as a single modality of care has been futile due to problems with drug solubility and compatibility between the drug classes.

Thus it would be desirable to have a nasal spray system allowing for two or more drugs to be stored separately and dispensed simultaneously through a single nasal dispensing device. The system of this invention is designed to overcome problems with potential drug interactions, solubility or incompatibilities while allowing for predetermined amounts of medications to be delivered at the desired target site. This invention overcomes these obstacles by creating an alternative delivery system.

These and other advantages of the present invention will be apparent from the following disclosure and claims taken in conjunction with the accompanying drawings.

SUMMARY OF THE INVENTION

The invention relates to a metered nasal spray dispensing device that allows for two aqueous preparations to be stored separately and be dispensed simultaneously as a single spray or mist at the desired target within the nasal airway. The medicaments are mixed instantaneously at the time of an actuation of the spray device as it leaves the spray nozzle. This allows for the simultaneous use of both medicaments without the pitfalls of potential interactions or incompatibilities between the two.

The preferred embodiment of the device consists of two separate storage chambers with each chamber having a conduit of continuity to a metered pump. Each pump is associated with a one way check valve to prevent reflux contamination from the medicine in the contra lateral chamber. A receptacle containing a conduit for each medicine permits the mixing of the two prior to leaving the spray nozzle. Thus, with each actuation of the spray each pump moves each medicament from its chamber through a micro check valve then into a receptacle and out a spray nozzle as part of a mixture of both medicaments in the form of a mist. The spray leaving the nozzle containing both medicaments is then deposited in the nasal airway at the desired target.

BRIEF DESCRIPTION OF THE DRAWINGS

For a more complete understanding of this invention reference can be made to the embodiment illustrated with the following text and drawings.

FIGS. 4A-4D are views of a third version employing syringe chambers.

DETAILED DESCRIPTION OF THE PREFERRED EMBODIMENT

As used herein, the following terms can be understood as follows:

Chamber refers to a closed compartment either collapsible (balloon, bag or syringe like) or rigid containing a liquid state of the medicament.

Pump refers to a mechanical device used to move the medication from the chamber.

Receptacle refers to a device that allows for a conduit of communication where medications meet prior to or during a spray actuation.

Capacitor refers to an expandable device used to compensate for back pressure in the system during pump use.

Check Valve refers to a mechanical device that facilitates unidirectional fluid flow.

Stylet refers to a rigid solid cylindrical shaped device that occupies dead space and provides support in a hollow elongated structure.

Figure 1:
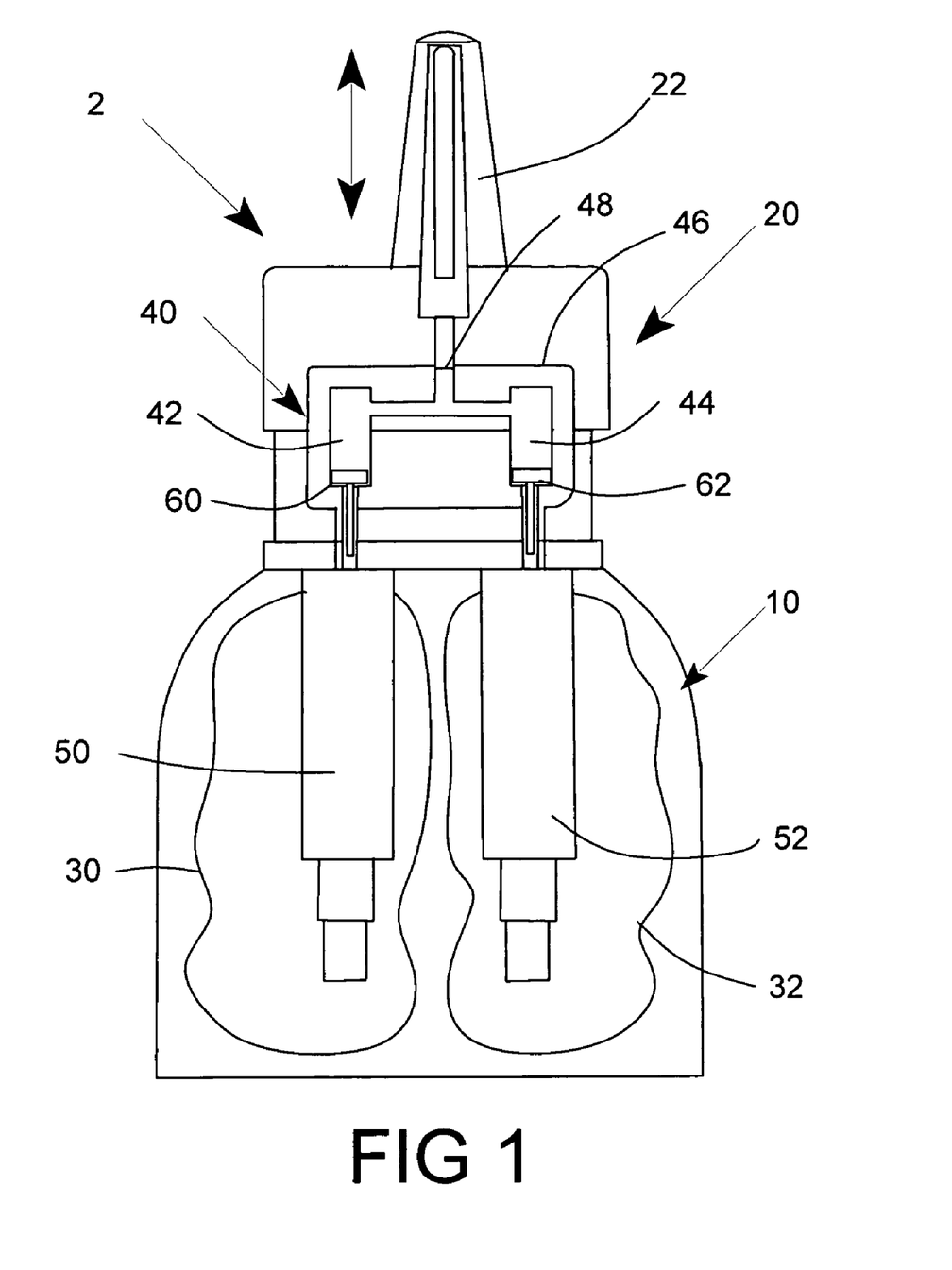
FIG. 1 is a side elevational view of a preferred embodiment of a nasal spray device of the present invention.
Figures 4A, 4B:
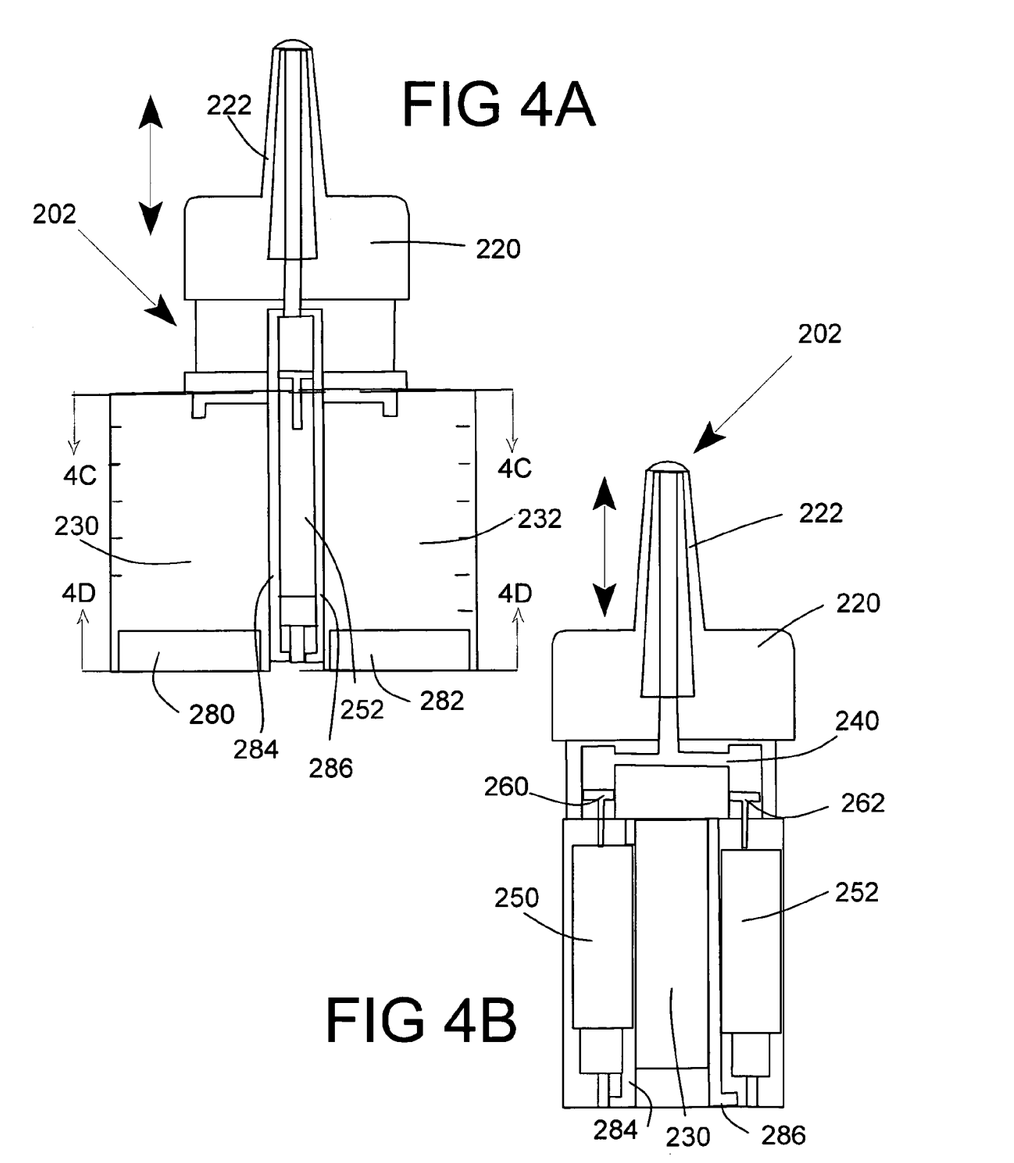
FIG. 4A is a front elevational view of the syringe version of this invention.
FIG. 4B is a side elevational view of the syringe version.
Figure 4C:
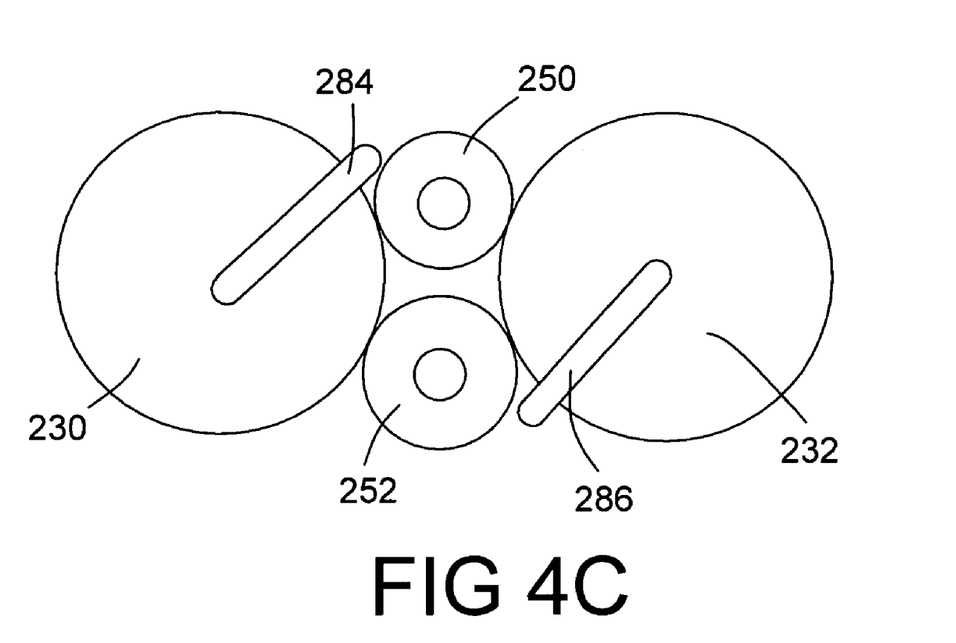
FIG. 4C is a cross section along section lines 4C-4C of FIG. 4A showing the top of the syringe version.
Figure 4D:
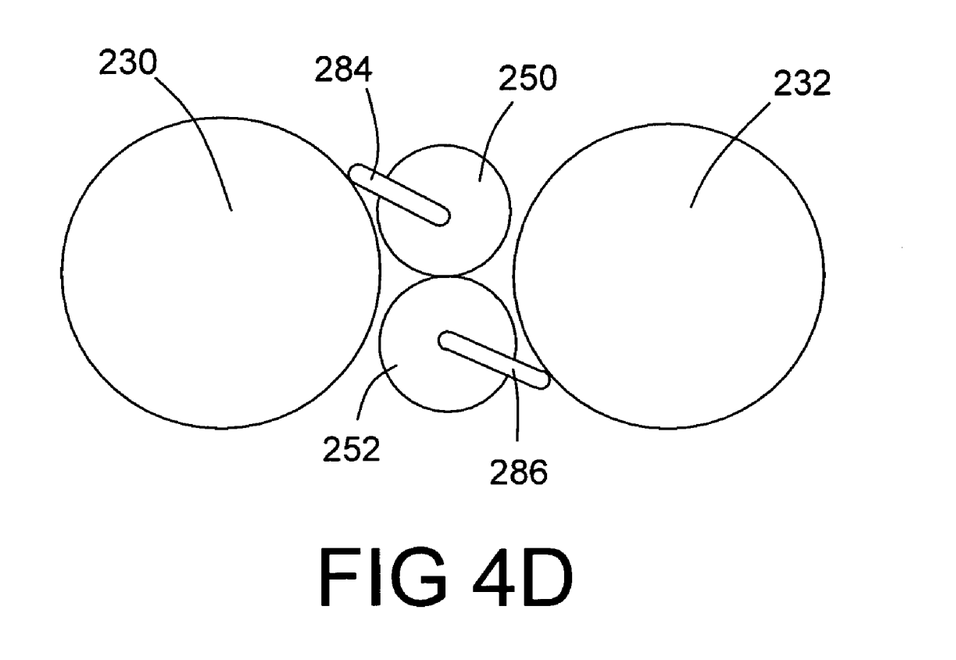
FIG. 4D is a cross section along section lines 4D-4D in FIG. 4A showing the intake at the bottom of the piston pumps.

Now referring FIG. 1, the preferred embodiment of a nasal spray apparatus 2 of the present invention is illustrated. In this embodiment there are two collapsible chambers 30, 32 in a surrounding rigid vented, but not necessarily air tight, housing or bottle 10. The venting of the housing or bottle 10 prevents a vacuum from developing in the housing 10. Each chamber 30, 32 is drained by a metered pump 50, 52 and has a sack, bag or bladder-like form that collapses as the liquid medicament is consumed or transported. The bottle or housing 10 may include an internal wall separating the two chambers. The chambers 30, 32 are preferentially vertically oriented. As seen in FIG. 1, each pump 50, 52 is connected to a single shared receptacle 40 formed in a spray nozzle 20. The receptacle 40 houses a check valve 60 for each pump 50, 52 and provides a conduit where two medicaments are initially mixed as the medicaments enter the spray nozzle 20. As seen in FIGS. 1 and 4, the receptacle 40 provides spaces 42, 44 for clearance for the check valves 60 to move from the closed position shown in FIG. 1 to an open position. Receptacle 40 also includes an internal passage 46 connecting spaces 42, 44 and a passage 48 leading to the spray tip 22 of spray nozzle 20. The nasal spray apparatus 2 can be activated by the user in the same what that a user would actuate a conventional nasal spray devices. The spray nozzle 20 is merely depressed relative to the bottle 10 to dispense the contents into the nasal passages of the user.

Figure 2:
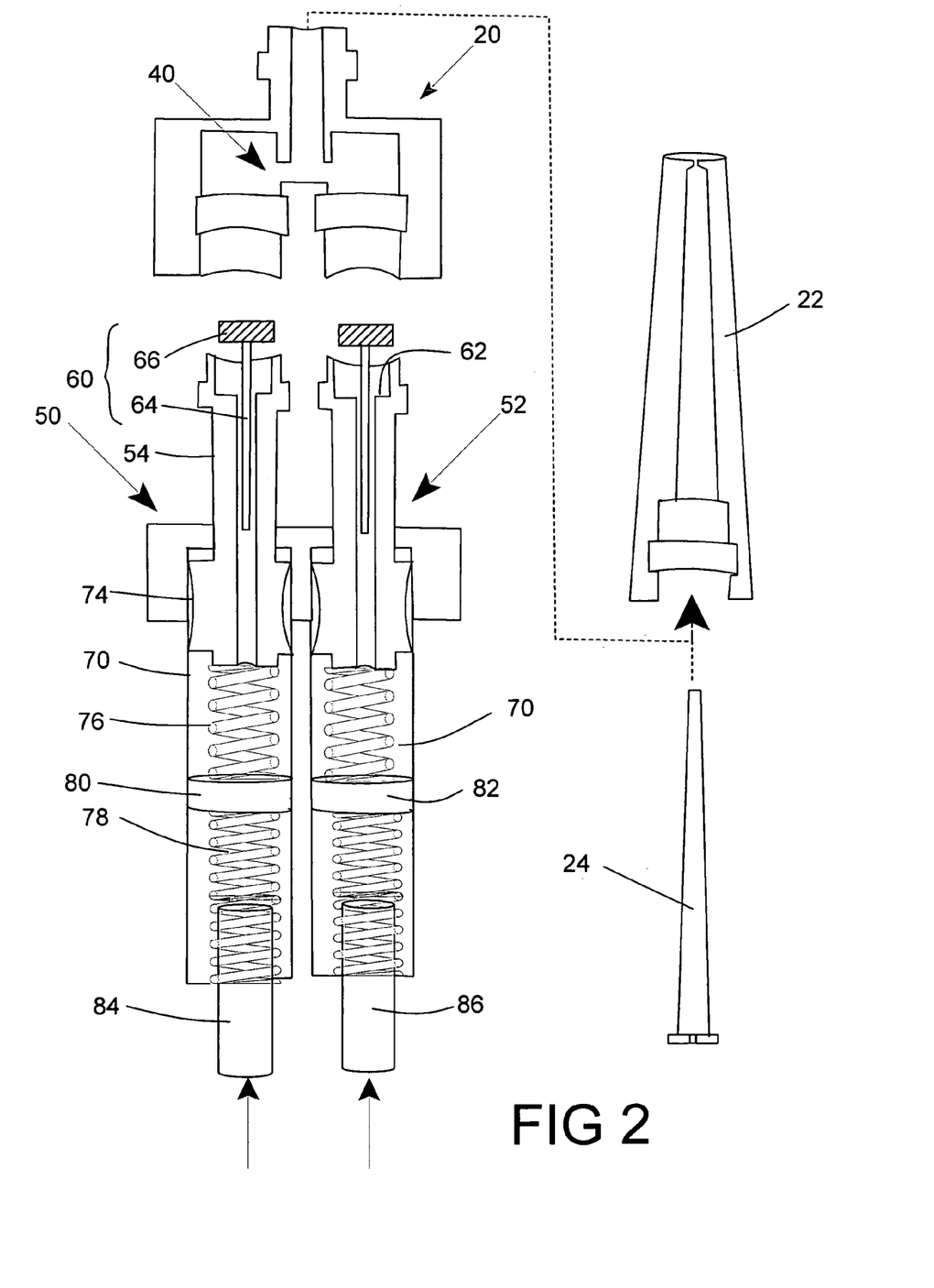
FIG. 2 is an exploded view showing details of the pump, receptacle and nozzle components.

FIG. 2 shows details of components for pumps 50, 52, receptacle 40 and spray nozzle tip 22 that can be employed with the embodiment of FIG. 1 as well as with other embodiments to be subsequently discussed in more detail. Each pump 50, 52 includes a pump housing 70, a vented plunger 74 with a plunger neck 54, stoppers 80 or 82 and two springs 76, 78. It should be understood that the drawings and embodiments are not necessarily to scale and serve as illustrative representations only. Indeed certain dimensional relationships are not to scale in order to illustrate important aspects of the invention, which would not be visible if the drawings were entirely to scale. While the complete embodiment of this invention is unique, a rather conventional pump including features of most metered spray pumps can be employed. The housing 70 contains a fixed predetermined volume to allow for a predetermined amount of medicament to be dispensed with each pump stroke. The top of each pump consists of the plunger 74 that is fenestrated. The fenestration allows for the passage of medicaments to leave the pumps 50,52 and pass through the check valves 60. Each check valve 60 comprises a check valve needle 66 and a check valve seat 62. The apex of the plunger is covered with a check valve needle 64 that slides in and out of the fenestration of the plunger 74 and into the receptacle 40 with pump action. This makes up a micro check valve configuration. The pin 64 has a smaller diameter than the opening or fenestration in the top of the plunger 74. Each check valve 60 includes a head 66 from which the pin 64 extends. When the check valve 60 moves to the open position shown in FIG. 2, the valve pin head 66 is spaced from a valve seat 62 on the top of the plunger 74 so that liquid medicament can flow through the opening between the check valves 60 and their respective seats 62. This particular feature of the pump design is unique. When depressing the pumps 50, 52, the check valve needle 64 rises and opens the check valve 60 to allow for medicament to pass from the pumps 50, 52 into the receptacle 40. The medicaments from each chamber 30, 32 are forced through the respective pumps and into the receptacle 40 during the down stroke of the pump plunger 74. First spring 76 forces the stopper 80, or 82 down to close off the respective intake hose 84 or 86, leading to chambers 30, 32, during the down stroke, so that only direction in which the liquid medicament previously stored in the pump housing 70 can flow is out the top of the respective piston pumps 50, 52. After multiple medicaments are mixed in the receptacle 40, the medicaments are forced through the spray nozzle tip 22 and into the user's nasal cavity. When the pump plunger is released, the spring action urges the pump plunger 74 upward closing the check valve 60. The second spring 78 urges the stopper upward opening the intake hoses 84, 86 communication with each separate chamber 30, 32. A vacuum is created in the pump housing 70 as the plunger 74 moves upward, and fluid medicaments from each chamber 30, 32 are drawn into the pump housing 70 of the respective pumps 50, 52. While this occurs, the check valves 60 prevent liquid medicament in the reservoir from passing back into the pumps 50, 52 from the receptacle 40 or adjacent pumps 50, 52 or chambers 30, 32 thereby minimizing cross contamination. Although the needle type check valve 60 employed in this embodiment is preferred, a variety of types of valves employing flaps or ball-like valves could also be employed.

The receptacle 40 attaches to the apex of each plunger tip (top of the pump). It contains a minimal low volume capacity to reduce storage of mixed medicaments in between nasal spray actuations. In the preferred embodiment the volume of the receptacle can be approximately 5-10 µl. This volume is far less than the volume of the individual pumps. The metered volume of medicament delivered by each pump 50, 52 will typically be about 50-100 µl. The receptacle 40 also serves as part of the housing of the micro check valve 60. The needle head 66 of the check valve 60 moves into the receptacle 40 with each pump action. The nozzle 20 of the spray contains a stylet 24 to minimize volume dead space, increase spray pressure and reduce storage of mixed medicament as well.

Figure 3:
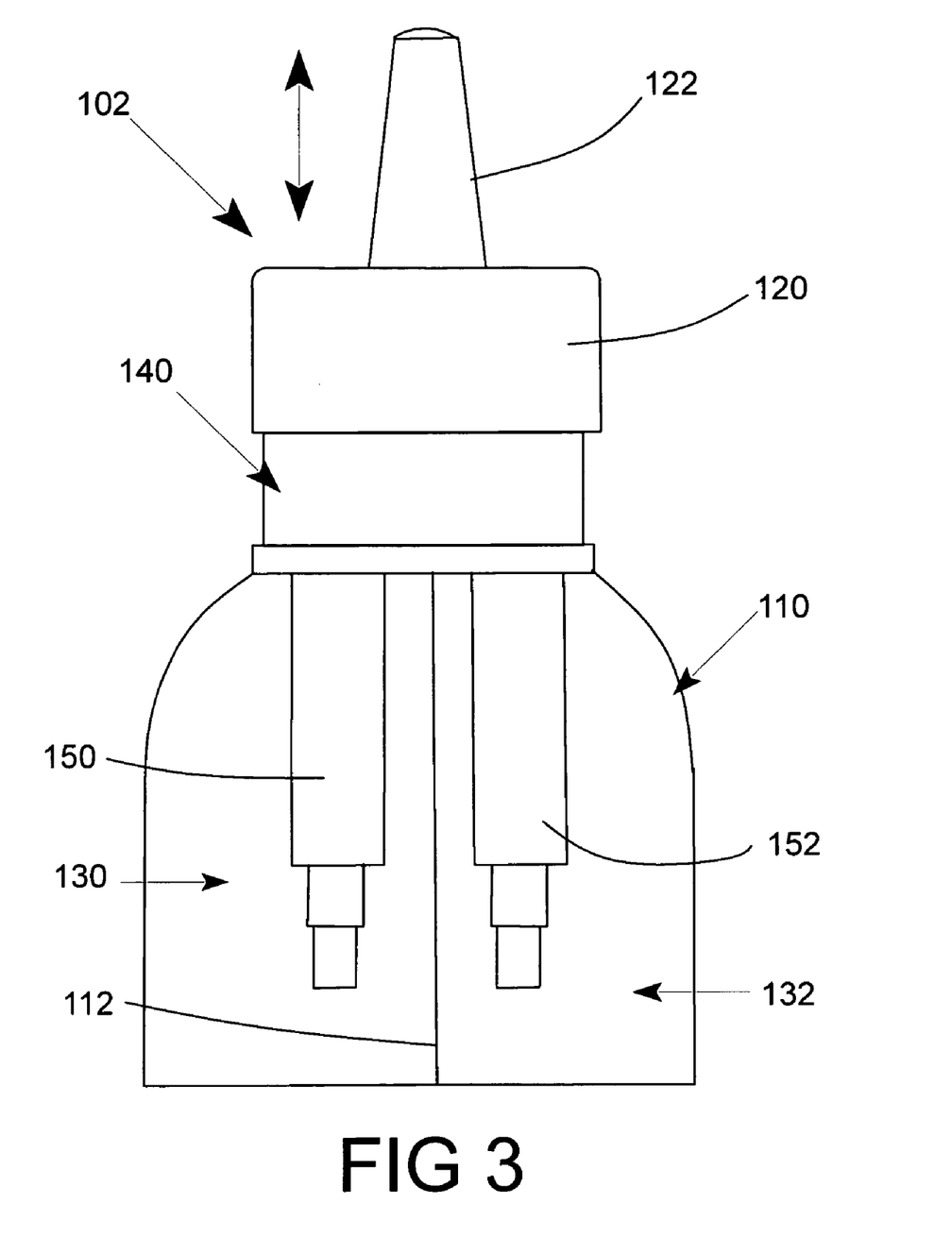
FIG. 3 is a side view of an alternate embodiment employing a bifurcated rigid container or bottle.

Several variations of collapsible or even rigid chambers may be employed in accordance with this invention. FIG. 3 shows a second spray apparatus 102 employing rigid closed chambers 130 and 132. A liquid tight wall 112 separates and creates the two chambers 130 and 132. Medicaments from each chamber are removed by the metered pumps 150 and 152. The piston pumps 150 and 152 can be identical to the pumps 50 and 52 employed with the embodiment of FIG. 1.

FIGS. 4A-4D show a third version 202 employing a collapsible syringe configuration including two syringe chambers 230 and 232. Stoppers 280 and 282 having an air/fluid interface moves vertically through a column formed by syringe chambers 230 and 232 as the medicament fluid is consumed. The stopper position as seen in FIG. 4A, when visualized though a semitransparent chamber walls that may serve as a indicator meter as well. The individual syringe chambers 230 and 232 can be located in an outer bottle that can also be transparent, or the syringe chambers can be located on the exterior of the device. Pumps 250 and 252 are positioned between the two syringe chambers 230 and 232 as seen in FIGS. 4C and 4D. In this embodiment, conduits 284 and 286 run from each pump 250, 252 to each chamber 230, 232 and ultimately joins the top of each chamber as shown in FIG. 4C. The conduits 284 and 286 extend along the exterior of corresponding chambers 230, 232 from openings located on top of each syringe chamber. These conduits are positioned along the external sides of the respective syringe chamber to the bottom of the respective piston type pump 250, 252. The connection of the conduits 284 and 286 to the pumps 250 and 252 is shown in FIG. 4D. Negative pressure generated with each pump action pulls the stoppers 280, 282 vertically towards the top of each chamber 230, 232 as the medicaments are dispensed from the inlets at the top of each corresponding chamber 230, 232 as seen in FIG. 4A. Each chamber would have been filled with liquid medicament in the absence of air. In FIGS. 4A-4D, both pumps are positioned between the chambers for space conservation purposes. A single spray nozzle 220 is mounted on the top of a housing containing a receptacle 240 in which the medicaments initially mix and which provides a passage to the spray tip 222. The reservoir of the receptacle 240 also provides space for check valves 260 and 262. The spray nozzle 220, the reservoir 240 and the check valves 260, 262 operate in the same manner as discussed with respect to the embodiments of FIGS. 1 and 3. The same corresponding components shown in FIG. 2 can also be employed in the embodiment of nasal spray device 202 shown in FIGS. 4A-4D.

Figure 5:
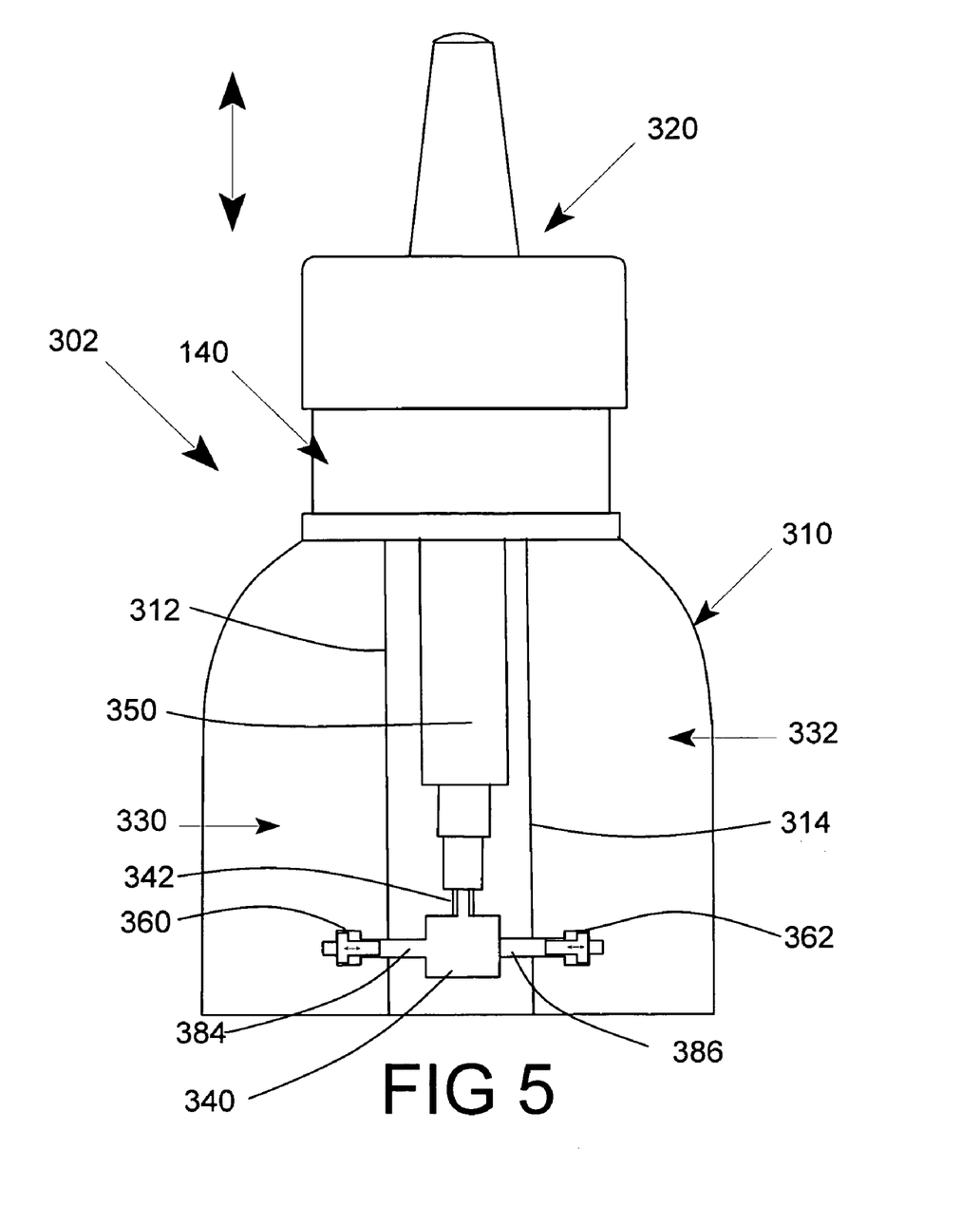
FIG. 5 is a side view illustrating an alternative preferred embodiment; whereas, the nasal spray device of the present invention employs a single pump system with dual chambers.

FIG. 5 illustrates an alternate embodiment of a nasal spray apparatus employing a single pump 350 to pump medicaments from two chambers 330, 332. This embodiment can be employed with medicaments that may be mixed in small amounts and retained for a period of time since a certain amount of mixed medicaments reside in the pump between actuations of the spray device. Conduits 384 and 386 communicate between the two chambers 330, 332 that are separated by water tight rigid walls 312 and 314 and check valves 360 and 362 on each side of the conduits 384, 386. Excessive cross-contamination is prevented by employing check valves 360, 362 that open and close the conduits 384, 386 providing an intake from each chamber 330, 332. A single receptacle 340 provides space for initially mixing the medicaments prior to entering a pump 350. A balloon capacitor 342 in the form of an expandable sleeve is located between the pump 350 and the receptacle 340 to compensate for back pressures generated by the pump 350 when the check valves 360, 362 close. The balloon capacitor 384 expands as the pump 350 is actuated to dispense mixed fluid-medicament residing in the pump 350 through the spray nozzle 320 into the user's nasal cavity. When the spray nozzle 320 is released, a negative pressure is generated within the pump 350, and this negative pressure causes the check valves 360, 362 to open. Medicaments from each chamber 230, 232 can then be drawn into the mixing reservoir 340 and then into the pump 350, where a metered dose of the mixed medicaments will be retained until the pump 350 is again actuated by depressing the spray nozzle 320.

Figure 6:
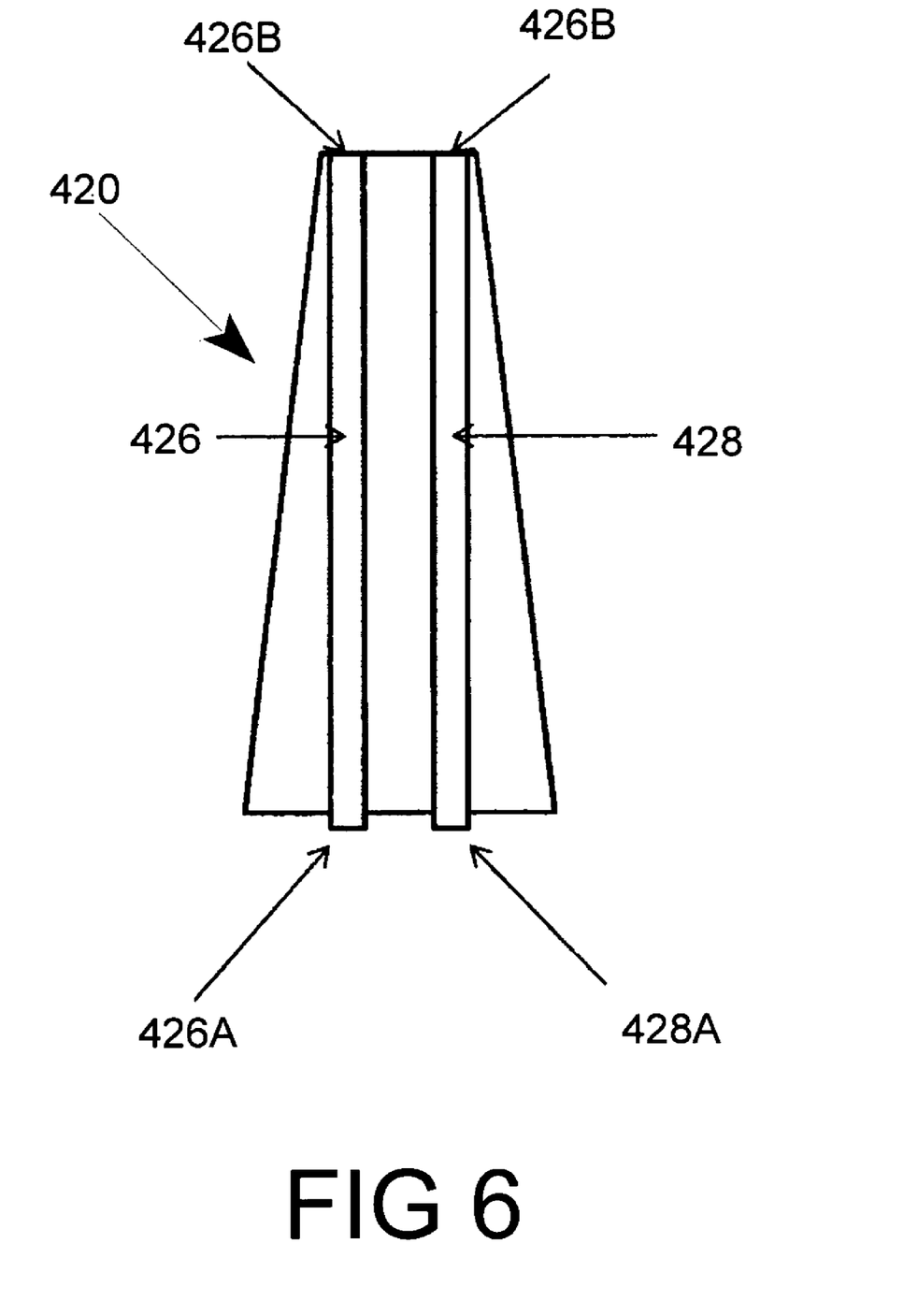
FIG. 6 is a side view illustrating another alternate embodiment of the present invention using a multi fenestrated nozzle tip.

FIG. 6 illustrates another embodiment in which each medicament is kept separate by means of any combination of the previous mentioned embodiments. In this embodiment two medicaments are not mixed in a reservoir. Instead the two medicaments are expelled through a system of multiple separate passages 426 and 428 extending through a nozzle spray tip 420. In this embodiment, intakes 426A and 428A are connected to the output from separate pumps, such as pumps 50, 52 in FIG. 2. The still separate medicaments are then separately dispensed through passage openings 426B and 428B into the user's nasal cavity.

The preferred embodiment of this invention shown in FIG. 1 has been successfully fabricated and tested. While specific embodiments of the present invention have been disclosed above, it will be appreciated that the invention is subject to modifications and variations within the broad scope of the invention. Therefore the present invention is defined in terms of the following claims and is not limited to the representative embodiments depicted and discussed herein.

I claim:

1. A nasal spray apparatus for simultaneously introducing at least two medicaments having incompatible properties into a user's nasal cavity, the nasal spray apparatus comprising:
   a spray nozzle configured for insertion of medicaments into a user's nasal cavity;
   two separate chambers for storing each of the two medicaments;
   a receptacle separate from the spray nozzle between the spray nozzle and the separate chambers in which the two medicaments first mix before being injected through the spray nozzle into the user's nasal cavity;
   two separate piston pumps for pumping each of the two medicaments from the separate chambers to the receptacle, the piston pumps and receptacle being configured so that medicaments having incompatible properties are mixed in prescribed concentrations immediately prior to injection through the spray nozzle into the user's nasal cavity,
   check valves positioned between the piston pumps and the receptacle, each check valve including a head that is shiftable into the receptacle to open the check valve, wherein
   the receptacle comprises a common receptacle located between the two separate piston pumps and the spray nozzle in which the at least two medicaments are first mixed, the common receptacle having a volume less than the volume of individual spray pumps so that only a relatively small volume of mixed medicaments can be retained in the receptacle after injection of metered doses of medications into the user's nasal cavity.

2. The nasal spray apparatus of claim 1 wherein separate piston pumps are positioned between each chamber and the receptacle.

3. The nasal spray apparatus of claim 1 wherein the spray nozzle is reciprocal relative to the piston pumps to pump the medicaments from the chambers through the piston pumps into the receptacle and to force medicaments after mixing into and through the spray nozzle in the user's nasal cavity.

4. The nasal spray apparatus of claim 3 wherein separate piston pumps are actuated by reciprocal movement of a single spray nozzle.

5. The nasal spray apparatus of claim 1 wherein the separate chambers are collapsible.

6. The nasal spray apparatus of claim 1 configured for injecting two medicaments have different viscosities into a user's nasal cavity.

7. The nasal spray apparatus of claim 1 configured for injecting two immiscible medicaments simultaneously into a user's nasal cavity.

8. The nasal spray apparatus of claim 1 configured for injecting a steroid and an antihistamine simultaneously into a user's nasal cavity.

9. A nasal spray apparatus for simultaneously introducing at least two medicaments having incompatible properties into a user's nasal cavity, the nasal spray apparatus comprising:
   a bottle including at least two storage compartments for separately storing the at least two medicaments;
   a spray nozzle for injecting the at least two medicaments into a user's nasal cavity as the medicaments are pumped from separate pumps communicating with separate storage compartments through the spray nozzle;
   wherein the at least two medicaments are mixed in a common receptacle within the nasal spray apparatus between the bottle and the spray nozzle as the at least two medicaments are pumped from the storage compartments through the spray nozzle in order to inject metered doses of the two medicaments in prescribed concentrations,
   check valves positioned between the piston pumps and the receptacle, each check valve including a head that is shiftable into the receptacle to open the check valve, and wherein
   the common receptacle is located between separate individual pumps and the spray nozzle in which the at least two medicaments are first mixed, the common receptacle having a volume less than the volume of individual spray pumps so that only a relatively small volume of mixed medicaments can be retained in the receptacle after injection of metered doses of medications into the user's nasal cavity.

10. The nasal spray apparatus of claim 9 wherein the storage compartments are collapsible.

11. The nasal spray apparatus of claim 9 wherein the two medicaments are injected in equal amounts into a user's nasal cavity.

* * * * *